US008414867B2

(12) United States Patent
Mueller-Walz et al.

(10) Patent No.: US 8,414,867 B2
(45) Date of Patent: *Apr. 9, 2013

(54) DRY POWDER FORMULATIONS

(75) Inventors: Rudi Mueller-Walz, Schopfheim (DE); Roland Steiner, Rheinfelden (CH)

(73) Assignee: Jagotec AG, Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/588,655

(22) Filed: Aug. 17, 2012

(65) Prior Publication Data

US 2013/0014758 A1    Jan. 17, 2013

Related U.S. Application Data

(60) Continuation of application No. 13/283,295, filed on Oct. 27, 2011, now Pat. No. 8,246,935, which is a continuation of application No. 12/536,998, filed on Aug. 6, 2009, now Pat. No. 8,211,405, which is a division of application No. 10/575,656, filed as application No. PCT/IB2004/003804 on Apr. 11, 2004, now abandoned.

(30) Foreign Application Priority Data

Nov. 14, 2003 (GB) .................................. 0326632.7

(51) Int. Cl.
A61K 9/00 (2006.01)
A61K 9/14 (2006.01)

(52) U.S. Cl. .......................................... 424/46; 424/489
(58) Field of Classification Search .................. 424/46, 424/489
See application file for complete search history.

(56) References Cited

U.S. PATENT DOCUMENTS

| | | | |
|---|---|---|---|
| 4,672,108 A | | 6/1987 | Kung et al. |
| 5,874,063 A | | 2/1999 | Briggner et al. |
| 5,981,719 A | | 11/1999 | Woiszwillo et al. |
| 6,136,563 A | | 10/2000 | Cunningham et al. |
| 6,182,655 B1 | | 2/2001 | Keller et al. |
| 6,521,260 B1 | * | 2/2003 | Staniforth ............. 424/490 |
| 6,528,096 B1 | | 3/2003 | Musa et al. |
| 6,645,466 B1 | * | 11/2003 | Keller et al. .............. 424/43 |
| 7,186,401 B2 | | 3/2007 | Keller et al. |
| 8,211,405 B2 | | 7/2012 | Mueller-Walz et al. |
| 8,246,935 B2 | | 8/2012 | Mueller-Walz et al. |
| 2003/0175214 A1 | | 9/2003 | Staniforth et al. |
| 2010/0144625 A1 | | 6/2010 | Mueller-Walz |
| 2011/0114092 A1 | | 5/2011 | Keller et al. |

FOREIGN PATENT DOCUMENTS

| | | |
|---|---|---|
| DE | 98022 A1 | 6/1973 |
| EP | 0239798 A1 | 10/1987 |
| EP | 0272772 A2 | 6/1988 |
| EP | 1129705 A1 | 9/2001 |
| JP | 2003034652 A | 2/2003 |
| WO | WO-9623485 A1 | 8/1996 |
| WO | WO-9703649 A1 | 2/1997 |
| WO | WO-9948476 A1 | 9/1999 |
| WO | WO-0028979 A1 | 5/2000 |
| WO | WO-0053157 A1 | 9/2000 |
| WO | WO 01/78693 * | 10/2001 |
| WO | WO-0178693 A2 | 10/2001 |
| WO | WO-0207705 A1 | 1/2002 |
| WO | WO-2004093848 A2 | 11/2004 |
| WO | WO-2005025540 A2 | 3/2005 |
| WO | WO-2005046636 A1 | 5/2005 |
| WO | WO-2007068443 A1 | 6/2007 |
| WO | WO-2008058691 A2 | 5/2008 |

OTHER PUBLICATIONS

Kassem. "Generation of Deeply Inspirable Clouds from Dry Powder Mixtures." Ph.D. Thesis, Dept. Pharmacy, King's College University of London. (1990).
Meakin et al. "Simulated 'in-use' and 'mis-use' Aspects of the Delivery of Terbutaline Sulphate from Bricanyl Turbohaler™ Dry Powder Inhalers." *Int. J. Pharm.* 119(1995):103-108.
Reynolds, ed. *Martindale: The Extra Pharmacopeia*. London: The Pharmaceutical Press. (1993):1442.
van Kamp et al. "The Role of Water Uptake on Tablet Disintegration." *Pharm. Acta Helv.* 61.1(1986):22-29.
Wade et al. eds. "Magnesium Stearate." *Handbook of Pharmaceutical Excipients*. London: The Pharmaceutical Press. (1994):280-282.
"Excipients: Lactose Monohydrate." www.pformulate.com'lactoserev.htm. Accessed Jun. 18, 2012.
Endo et al. "Erythritol-Based Dry Powder of Glucagon for Pulmonary Administration." Int. J. Pharm. 290(2005):63-71.
Ohmori et al. "Development of Dry Powder Inhalation System of Novel Vasoactive Intestinal Peptide (VIP) Analogue for Pulmonary Administration." *Life Sci.* 79.2(2006):138-143.
Peart. "Electrostatic Charge Interactions in Pharmaceutical Dry Powder Aerosols." (1996).
GB Research Report dated Mar. 23, 2004, corresponding to GB0326632.7.
International Search Report mailed Mar. 30, 2005, corresponding to PCT/IB/2004/003804.
Meakin et al. "The Effect on Flow Rate on Drug Delivery from the Pulvinal, a High-Resistance Dry Powder Inhaler." J. Aero. Med. 11.3(1998):143-152.
Peart et al. "Multicomponent Particle Interactions in Dry Powder Aerosols." *Pharma. Res.* 14.S11(1997):S142-S143. (Abstract #1405).
Staniforth et al. "Interparticle Forces in Binary and Ternary Ordered Powder Mixes." J. Pharm. Pharmacol. 34.3(1982):141-145.
Clenil Compositum Polvere. Repertoro Farmaceutico Italiano. Milan: Framindustria: Associazione Nazionale dell'Industraia Farmaceutica. (1989):303-305. (Partial English Translation Included) only translation of clenil composition.

* cited by examiner

*Primary Examiner* — Ileana Popa
*Assistant Examiner* — Genevieve S Alley
(74) *Attorney, Agent, or Firm* — Mintz Levin Cohn Ferris Glovsky and Popeo, P.C.; Muriel Liberto, Esq.

(57) ABSTRACT

A dry powder suitable for inhalation in a dry powder inhaler, the powder comprising a carrier, an active agent and at least 0.5% by weight of magnesium stearate, the powder being further characterized in that the less than 10% of the surface of the carrier material is covered with particles of magnesium stearate. The invention is also directed to a method of making dry powders by blending together the ingredients mentioned in a diffusion blender for a period of time that is less than 60 minutes.

18 Claims, No Drawings

DRY POWDER FORMULATIONS

The present invention is concerned with dry powder formulations for use in dry powder inhalers.

Dry Powder inhalers (DPIs) represent an alternative to Metered Dose Inhalers (MDIs) for the administration of medicaments to the lung.

Active substances for use in dry powders for inhalation must be provided in the form of very fine particles in order that they can penetrate deep within the lung. Indeed, if the lung is to be used to administer drug substances systemically, the active substance must be sufficiently fine that it penetrates into the alveolar ducts and sacs whereupon it can be most efficiently absorbed into the blood.

However, fine particulates can present major formulation difficulties. For example such particulates possess strong adhesive and cohesive properties that can cause the active particles to aggregate and can lead to poor bulk properties of the powder such as poor flowability.

The mechanical properties of dry powders can be improved by mixing the fine particles of active substance with relatively coarser particles of an inert carrier material. The ordered mixture of carrier and active enables the dry powder to be handled more easily during manufacture and during filling of the powder into DPI devices. Additionally, the active substance is maintained in a relatively dispersed state on the surface of the carrier particles. However, the adhesive force between carrier and active must not be so great that upon actuation of the DPI the efficient and reproducible re-dispersion of the active into fine dispersible particles is prevented.

A common approach used by formulators to achieve an appropriate balance between the competing forces of adhesion and re-dispersion is to treat the carrier with a ternary component in order to cover or coat the carrier particles and thereby modulate the adhesive force between the active particles and the carrier surface.

Numerous ternary components have been suggested in the art. There are still further suggestions in the prior art as to the amount of ternary component that should be employed, and the extent to which the ternary component must coat or cover the carrier surface in order to achieve an appropriate compromise between adhesion and re-dispersion such that active particles are not liable to prematurely segregate from the carrier surface (e.g. during storage and handling), but are readily released upon actuation initiated and driven in passive dry powder inhalers by a patient's inspiration.

U.S. Pat. No. 6,521,260 describes the use of ternary components in dry powder formulations containing active and carrier. The nature and amount of ternary component is selected in order to alter the surface properties of the carrier with the purpose of promoting release of active particles upon actuation of an inhaler. However, the amount of ternary component must not be so great such that active and carrier particles prematurely segregate during storage.

This reference mentions that surface active materials may be employed as ternary components. In this regard magnesium stearate may be used but it is stated clearly that it is not preferred. This reference does not state how much magnesium stearate should be employed to achieve the purpose of promoting release of the active upon actuation. We are told only that 1.5% by weight of magnesium stearate is too much as it promotes premature segregation. The only other comment relating to the use of magnesium stearate is that it is highly surface active and should be used only in "particularly small amounts". By contrast, phosphatidyl cholines, being less surface active than magnesium stearate can be used in higher quantities. Conspicuously, this reference exemplifies a formulation employing lecithin (a natural mixture of phosphatidyl cholines) in an amount of 0.5% by weight.

Insofar as the skilled person would be motivated to use magnesium stearate despite the clear prejudice towards its use, it would be employed in only a "particularly small amount" relative to the 0.5% by weight suggested for lecithin and other less surface active materials Indeed in a paper (J. Pharm. Pharmacol. 1982, 34: 141-145, a named inventor on U.S. Pat. No. 6,521,260 teaches that magnesium stearate can affect the adhesion of active substances to carrier particles, and that its use in amounts of 0.5% to 4.0% by weight de-stabilises formulations to the extent that significant segregation occurs.

The benefits of using magnesium stearate in dry powders is taught in U.S. Pat. No. 6,528,096. Specifically it teaches that it can be used to alter the surface properties of carrier particles and thereby improve the properties of dry powder formulations. However, the skilled person is informed that it should be used in amounts of less than 0.5% by weight, and no significant improvement in the fine particle fraction of a delivered dose is achieved with concentrations above 0.25% by weight. Additionally, this reference reports an "advantageous relationship" between the degree of carrier surface coating by magnesium stearate and the respirable fraction of a delivered dose. Critical to the working of this invention is the need to ensure a continuous coating of magnesium stearate over more than 10% of the surface of the carrier particles. The requisite coating can be achieved by conventional blending of carrier and magnesium stearate, or alternatively higher shear mixing techniques can be employed. High shear mixing can achieve the requisite coating within about 0.5 hours, however, the skilled person is clearly taught that if conventional blending is to be employed the blending time must be in excess of 2 hours.

In The Journal of Aerosol Medicine Vol 11, No. 3, 1998 at 143-152, an inventor of U.S. Pat. No. 6,528,096 teaches that pre-treatment of lactose particles with 0.25% magnesium stearate significantly improves the disaggregation of beclamethasone dipropionate without causing segregation during filling, transport or use.

It is clear from the prior art that any beneficial properties that derive from the use of magnesium stearate are predicated on its apparent ability to alter the surface properties of carrier particles. In this regard, the skilled person is taught that in order to advantageously influence the fine particle fraction of a delivered dose, as high a surface coating should be obtained with as little magnesium stearate as possible.

Certain mixing techniques are taught for achieving this result, which involve either high energy mixing, or long duration low energy mixing. Other suggestions involve combining low energy blending coupled with carrier treatment steps involving high energy milling or mixing.

The problem with the suggestions made in the prior art is that no consideration is given to the nature of the active substance employed, and the constraints that the physical and chemical properties can impose on the amounts of magnesium stearate that can be used in practice. For example, it is known that dry powders are sensitive to atmospheric humidity, and are difficult to use for that reason in multi-dose dry powder inhaler devices. It is also known that many active substances can be hygroscopic and can exacerbate the moisture sensitivity of dry powders. Dry powders for inhalation should be excluded from humid conditions to the greatest extent possible. Moisture sensitivity is often manifested in a dramatic reduction of the inhalable proportion of an emitted dose (the so-called "fine particle fraction"), which can be determined according to in-vitro measurements described below. Moisture can also influence adversely the accuracy and reproducibility of shot weight and emitted dose content uniformity.

The use of magnesium stearate to improve the moisture resistance of dry powders is described in WO 00/28979.

It is not only the hygroscopic nature of certain active substances that can have a destabilsing effect on dry powders. The amount of active substance that needs to be delivered in a single inhalation by from a DPI device is dictated by the medical condition that is intended to be treated, and in certain situations the drug loading can be quite high. This can also adversely affect the mechanical properties of dry powders, e.g. flowability, absent the use of sufficient magnesium stearate, e.g. for lubricating purposes.

Accordingly, whereas the prior art teaches the skilled person that only small amounts, i.e. less than 0.5% magnesium stearate can be tolerated in dry powder formulations, this is generally an unacceptably low amount taking into consideration the demands imposed by the quantity and properties of the active substance employed.

Applicant has surprisingly found that the effect of surface coverage of magnesium stearate on the performance of dry powders appears to be minor compared to the moisture protection and lubricating properties of this substance, in terms of the uniformity of the delivered dose and the fine particle fraction of the delivered dose. Accordingly, provided one ensures that during the preparation a dry powder for inhalation the surface coverage of the carrier particles by magnesium stearate is kept low, one can employ relatively large amounts of magnesium stearate and yet obtain reproducibly high fine particle fraction, even after prolonged periods of storage, and through life of a device.

Accordingly, in a first aspect the invention provides a dry powder for inhalation comprising active particles and carrier particles for supporting active particles, the formulation further containing magnesium stearate in an amount of at least 0.5% by weight of the formulation, and wherein particles of magnesium stearate are disposed on the surface of the carrier particles such that the surface coverage of carrier particles is less than 10%.

The amount of magnesium stearate employed should be at least 0.5% by weight. The upper limit depends on the toxicological acceptability of large amounts of magnesium stearate delivered to the lungs. A level of up to 2.0% is preferred. Within these limits, the amount of magnesium stearate employed will depend on the nature of the active substance, and the amount to be employed. The skilled person will have regard the physical and chemical properties of the active substance and be able to select an appropriate amount without undue burden or without having to resort to inventive activity.

In a particular embodiment the magnesium stearate may be employed in an amount of 0.5 to 2.0% by weight, more particularly 0.5 to 1.5% by weight, still more particularly 0.5 to 1.0% by weight, even more particularly 0.6 to 1.0% by weight.

The extent to which the magnesium stearate covers the surface of the carrier particles can be determined from scanning electron microscope (SEM) images. Scanning electron microscopy is one of the most versatile analytical techniques and it is well known in the art. Compared to conventional optical microscopes, an electron microscope offers advantages including high magnification, large depth of focus, great resolution and ease of sample preparation and observation. Electrons generated from an electron gun enter a surface of a sample and generate many low energy secondary electrons. The intensity of these secondary electrons is governed by the surface topography of the sample. An image of the sample surface is therefore constructed by measuring secondary electron intensity as a function of the position of the scanning primary electron beam.

Such microscopes may be equipped with an EDX analyzer (an Electron Dispersive X-ray analyzer), that can produce an image selective to certain types of atoms, for example magnesium atoms. In this manner it is possible to obtain a clear data set on the distribution of magnesium stearate on the surface of carrier particles.

Backscattered electron (BSE) imaging and Energy Dispersive X-ray (EDX) analysis are used for chemical analysis. The intensity of backscattered electrons generated by electron bombardment can be correlated to the atomic number of an element within a sampling volume. Hence, qualitative elemental information can be revealed. The characteristic X-rays emitted from a sample serve as fingerprints and give elemental information of samples that can be as a semi-quantitative analysis, a quantitative analysis, line profiling and spatial distribution of elements. SEM with X-ray analysis is an efficient, inexpensive, and non-destructive surface analysis method.

In order to carry out BSE and EDX measurements, dry powder particles are typically scattered onto a medium such as a carbon tape, and the tape is then shadowed with gold or platinum prior to analysis. Analysis is then carried out on a representative sample of particles of the powder.

BSE provides information on the atomic contrast within a sample. In BSE images high atomic number elements appear as bright spots whereas low atomic number elements are dark. This contrast gives further information as to the position different elements on the sample, and therefore the nature and extent of coverage of magnesium stearate are revealed.

EDX provides an X-ray mapping for chosen elements. In this way, one can see where on the sample material magnesium atoms (and therefore magnesium stearate) are concentrated.

In this manner it can be shown that the magnesium stearate forms aggregates on the surface of the carrier particles. These aggregates cannot be considered as forming a surface "coating" in any conventional meaning of the word. It is also clear that the aggregates cover less than 10% of the surface even with relatively high loadings of magnesium stearate, e.g. 2% by weight. More particularly the coverage is less than 5%, still more particularly less than 2%, e.g. from 0.5 to 2%.

Contrary to the teaching in U.S. Pat. No. 6,528,096 that it is advantageous to obtain the highest surface coverage possible (and in any event greater than 10%) to achieve a better respirable fraction, applicant has found that low coverage, below 10% is required. In fact by using particular mixing conditions, it is possible to achieve very low coverage notwithstanding that high amounts of magnesium stearate, i.e. 0.5% at least are employed.

The formulations of the present invention are prepared in a manner to ensure the lowest possible coverage of magnesium stearate on the carrier particles.

Accordingly, the invention provides in another of its aspects a method of producing dry powder formulations comprising the step of blending carrier material with magnesium stearate in a powder blender. Such powder blenders include diffusion blenders and tumble blenders.

Applicant has found that one can improve the fine particle fraction of a delivered dose of a dry powder, if the method of forming the powder is relatively low energy and of short duration. Preferably, the blending operation is carried out by diffusion blending, which is an operation whereby different particles are reoriented in relation to one another when they are placed in random motion, and the interparticle friction is reduced as a result of bed expansion. Bed expansion is achieved using a rotating container. Suitable powder blenders or diffusion blenders are primarily distinguished by their geometric shapes and position of the axis of rotation. Suitable diffusion blenders may be selected from the group consisting of V-blenders, Double-cone Blenders, Slant Cone Blenders, Cube Blenders, Bin Blenders, Horizontal or Vertical Drum Blenders, Static Continuous Blenders, and Dynamic Continuous Blenders.

Diffusion blenders suitable for use in the present invention preferably operate under a low energy consumption, such as 0.1-1 kW per 100 liters. The period of blending should not exceed one hour and preferably is less than 30 minutes, more particularly less than 20 minutes, for example about 15 to 20 minutes.

The applicant has found that low energy mixing for the shortest possible time has the primary function of ensuring low surface coverage, notwithstanding the relatively high amounts of magnesium stearate that are employed. In addition, low energy, short duration mixing reduces the amount of energy fed into the powder and therefore reduces the possibility of de-mixing of the powder.

As is well known to the person skilled in the art, powder blenders are distinct from high shear mixing equipment such as convection mixers that operate on the principle of reorienting particles as a result of mechanical movement (e.g. paddle or plow mixing), or pneumatic mixing whereby particles are re-orientated as a result of the expansion of a powder bed by gas.

High shear mixers generally work with an energy consumption orders of magnitude higher than powder blenders (e.g. 10-100 kW/100 liters), and so exert a much higher shear force, thereby introducing much higher energy into the powders, which may have the effect of agglomerating the particles of active substance.

The blending step described above is preferably carried out as one of a series of blending steps described below.

In a first step, carrier and magnesium stearate are mixed in a powder blender, for a period not exceeding one hour and preferably less than 30 minutes, more particularly less than 20 minutes, for example about 15 to 20 minutes.

In a second step the mixture from the first step is mixed in a powder blender with the active substance, for a period not exceeding one hour and preferably less than 30 minutes, more particularly less than 20 minutes, for example about 15 to 20 minutes.

If the amount of active substance used in the mixture is low, e.g. less than about 30% by weight of the composition, more particularly about 0.01 to 10% by weight of the composition, it is preferred that after the first step, a small portion of the mixture, e.g. about 10% of the mixture is mixed with the active substance in the second step, to four a powder mixture relatively concentrated with respect to the active substance. This is to ensure adequate mixing of the active substance with the carrier material.

Subsequently, a third blending step is employed to mix the remaining material from step 1 with the concentrated mixture from step 2 in a powder blender, for a period not exceeding one hour and preferably less than 30 minutes, more particularly less than 20 minutes, for example about 15 to 20 minutes.

It is preferred that no other blending step is carried out. Furthermore, no high shear mixing or milling steps should be carried out in relation to any of the powder ingredients if improvements in fine particle fraction are to be observed. However, to ensure the powder ingredients are of the appropriate particle size it is customary to prepare the ingredients by screening through appropriate sized sieves, e.g. 25 to 500 micrometer size (500 to 30 mesh according to BS 410), more particularly 63 to 250 micrometer (240 to 60 mesh according to BS 410).

The rotation of the blender may be suitably carried out at a speed in the range of from 20 rpm to 120 rpm, preferably, from 50 rpm to 100 rpm.

Where the concentration of active ingredient in the final formulation is low, e.g. less than 5% w/w, it may be convenient to prepare the formulation by blending the active substance with an amount of magnesium stearate in the range of from 10% to 50% of the final amount, suitably of from 15% to 45%, preferably of from 20% to 40%, after which the remainder of the magnesium stearate is added.

The active substance may be practically any pharmaceutically active compound which can be administered by inhalation in dry powders.

Active substances may be chosen from beta-mimetics such as Levalbuterol, Terbutalin, Reproterol, Salbutamol, Salmeterol, Formoterol, Fenoterol, Clenbuterol, Bambuterol, Tulobuterol, Broxaterol, Epinephrin, Isoprenaline or Hexoprenaline; an Anticholinergic such as Tiotropium, Ipratropium, Oxitropium or Glycopyrronium; a Corticosteroid, such as Butixocart, Rofleponide, Budesonide, Ciclosenide, Mometasone, Fluticasone, Beclomethasone, Loteprednol or Triamcinolone; a Leukotrienantagonist, such as Andolast, Iralukast, Pranlukast, Imitrodast, Seratrodast, Zileuton, Zafirlukast or Montelukast; a Phosphodiesterase-Inhibitor, such as Filaminast or Piclamilast; an PAF-Inhibitor, such as Apafant, Forapafant or Israpafant; a potassium channel opener such as Amiloride or Furosemide; a pain killer such as Morphine, Fentanyl, Pentazocine, Buprenorphine, Pethidine, Tilidine, Methadone or Heroin; a potency agent such as Sildenafil, Alprostadil or Phentolamine; or a pharmaceutically acceptable derivative or salt of any of the foregoing compounds or classes of compounds. In as much as any of these compounds possess chiral centres, the compounds can be used in optically pure form, or can be presented as diastereomeric mixtures or racemic mixtures.

Dry powders of the present invention may also employ proteins, peptides, oligopeptides, polypeptides, polyamino acids nucleic acid, polynucleotides, oligonucleotides and high molecular weight polysaccharides.

Examples of macromolecules that find use in the present invention are:

Albumins (preferably, human serum Insulin; albumin); BSA; IgG; IgM; insulin; GCSF; GMCSF; LHRH; VEGF; hGH; lysozyme; alpha-lactoglobulin; basic fibroblast growth factor basic fibroblast growth factor; (bFGF); asparaginase; tPA; urokinase-VEGF; chymotrypsin; trypsin; streptokinase; interferon; carbonic anhydrase; ovalbumin; glucagon; ACTH; oxytocin; phosphorylase b; alkaline phosphatase-secretin; vasopressin; levothyroxin; phatase; beta-galactosidase; parathyroid hormone, calcitonin; fibrinogen; polyaminoacids (e.g., DNAse, alphal antitrypsin; polylysine, polyarginine); angiogenesis inhibitors or pro-immunoglobulins (e.g., antibodies); moters; somatostatin and analogs; casein; collagen; gelatin; soy protein; and cytokines (e.g., interferon, interleukin); immunoglobulins;

Physiologically active proteins such as peptide hormones, cytokines, growth factors, factors acting on the cardiovascular system, factors acting on the central and peripheral nervous systems, factors acting on humoral electrolytes and hemal substances, factors acting on bone and skeleton, factors acting on the gastrointestinal system, factors acting on the immune system, factors acting on the respiratory system, factors acting on the genital organs, and enzymes;

Hormones and hormone modulators including insulin, proinsulin, C-peptide of insulin, a mixture of insulin and C-peptide of insulin, hybrid insulin cocrystals (Nature Biotechnology, 20, 800-804, 2002), growth hormone, parathyroid hormone, luteinizing hormone-releasing hormone (LH-RH), adrenocorticotropic hormone (ACTH), amylin, oxytocin, luteinizing hormone, (D-Tryp6)-LHRH, nafarelin acetate, leuprolide acetate, follicle stimulating hormone, glucagon, prostaglandins, estradiols, testosterone, and other factors acting on the genital organs and their derivatives, analogues and congeners. As analogues of said LH-RH, such known substances as those described in U.S. Pat. Nos. 4,008,209, 4,086,219, 4,124,577, 4,317,815 and 5,110,904 can be mentioned;

Hematopoietic or thrombopoietic factors include, among others, erythropoietin, granulocyte colony stimulating factor (G-CSF), granulocyte-macrophage stimulating factor (GM-CSF) and macrophage colony stimulating factor (M-CSF), leukocyte proliferation factor preparation (Leucoprol, Morinaga Milk), thrombopoietin, platelet proliferation stimulating factor, megakaryocyte proliferation (stimulating) factor, and factor VIII;

Therapeutic factors acting on bone and skeleton and agents for treating osteoporosis including bone GLa peptide, parathyroid hormone and its active fragments (osteostatin, Endocrinology 129, 324, 1991), histone H4-related bone formation and proliferation peptide (OGP, The EMBO Journal 11, 1867, 1992) and their muteins, derivatives and analogs thereof;

Enzymes and enzyme cofactors including pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, and superoxide dismutase (SOD);

Vaccines include Hepatitis B, MMR (measles, mumps, and rubella), and Polio vaccines;

Growth factors include nerve growth factors (NGF, NGF-2/NT-3), epidermal growth factor (EGF), fibroblast growth factor (FGF), insulin-like growth factor (IGF), transforming growth factor (TGF), platelet-derived cell growth factor (PDGF), and hepatocyte growth factor (HGF);

Factors acting on the cardiovascular system including factors which control blood pressure, arteriosclerosis, etc., such as endothelins, endothelin inhibitors, endothelin antagonists described in EP 436189, 457195, 496452 and 528312, JP [Laid Open] No. H-3-94692/1991 and 130299/1991, endothelin producing enzyme inhibitors vasopressin, renin, angiotensin I, angiotensin II, angiotensin III, angiotensin I inhibitor, angiotensin II receptor antagonist, atrial naturiuretic peptide (ANP), and antiarrythmic peptide;

Factors acting on the central and peripheral nervous systems including opioid peptides (e.g. enkephalins, endorphins), neurotropic factor (NTF), calcitonin gene-related peptide (CGRP), thyroid hormone releasing hormone (TRH), salts and derivatives of TRH [JP [Laid Open]No. 50-121273/1975 (U.S. Pat. No. 3,959,247), JP [Laid Open]No. 52-116465/1977 (U.S. Pat. No. 4,100,152)], and neurotensin;

Factors acting on the gastrointestinal system including secretin and gastrin;

Factors acting on humoral electrolytes and hemal substances including factors which control hemagglutination, plasma cholesterol level or metal ion concentrations, such as calcitonin, apoprotein E and hirudin. Laminin and intercellular adhesion molecule 1 (ICAM 1) represent exemplary cell adhesion factors;

Factors acting on the kidney and urinary tract including substances which regulate the function of the kidney, such as brain-derived natriuretic peptide (BNP), and urotensin;

Factors which act on the sense organs including factors which control the sensitivity of the various organs, such as substance P;

Chemotherapeutic agents, such as paclitaxel, mytomycin C, BCNU, and doxorubicin;

Factors acting on the immune system including factors which control inflammation and malignant neoplasms and factors which attack infective microorganisms, such as chemotactic peptides and bradykinins; and Naturally occurring, chemically synthesized or recombinant peptides or proteins which may act as antigens, such as cedar pollen and ragweed pollen, and these materials alone or together with coupled to haptens, or together with an adjuvant.

The present invention is particularly useful in the formulation of moisture sensitive active substances, such as any compounds mentioned above that are in salt form such as a chloride, bromide, iodide, nitrate, carbonate, sulphate, methylsulphate, phosphate, acetate, benzoate, benzensulphonate, fumarate, malonate, tartrate, succinate, citrate, lactate, gluconate, glutamate, edentate, mesylate, pamoate, pantothenate or hydroxynaphthoate; or an ester foam such as an acetate, propionate, phosphate, succinate or etabonate.

Formulations containing a beta-mimetic, an anti-cholinergic or a corticosteroid, alone or in any combination thereof constitute particular embodiments of the present invention. These actives may be present in salt or ester form, such as a beta-mimetic in salt form, e.g. levalbuterol sulphate, formoterol fumarate, formoterol tartrate, salbutamol sulphate or salmeterol xinafoate (salmeterol 1-hydroxy-2-naphthoate); an anti-cholinergic in salt form such as oxitropium bromide, glycopyrronium bromide, ipratropium bromide or tiotropium bromide; or a corticosteroid in the form of an ester, such as beclamethasone dipropionate, fluticasone propionate, triamcinoline 16,21-diacetate, triamcinoline acetonide 21-acetate, triamcinoline acetonide 21-disodium phosphate, triamcinoline acetonide 21-hemisuccinate, mometasone furoate, or loteprednol etabonate.

In order that the active substance is inhalable, i.e. it can pass into the deep lung such as the terminal and respiratory bronchioles and the alveolar ducts and sacs, it must be in particulate form having a mean particle diameter (measured as the mass mean aerodynamic diameter) of at most about 10 microns, e.g. from 1 to 10 microns, and preferably 1 to 6 microns. Such microfine particles can be obtained in a manner known per se, for example by micronisation, controlled precipitation from selected solvents, or by spray drying.

The amount of active substance employed may vary within wide limits depending on the nature of the active substance, the type and severity of the condition to be treated and the condition of the patient in need of treatment.

For active substances employed to treat local conditions of the lung such as all manner of asthma and chronic obstructive pulmonary disease, relatively low doses of active substance can be employed, for example about 5 to 5000 micrograms, more particularly 5 to 500 micrograms.

For active substances that are intended to be delivered systemically through the lung, one may need higher doses to take into account issues relating to absorption through the lung and into the blood plasma. Typically, one might employ active substances at levels of about 20 micrograms to 50 milligrams, more particularly 50 micrograms to 20 milligrams.

Expressed as a concentration based on the total weight of the formulation, the active substance may be present in amounts of 0.01 to 30% by weight, more particularly 0.1 to 10% by weight, more particularly 0.1 to 5% by weight. It is not surprising therefore that to achieve dosage accuracy, the active substance must be diluted with carrier material. In a typical formulation the carrier material may be present in amounts of up to 99% by weight or more, in particular 50 to 99% by weight, depending on the particular dilution desired and on the amount of magnesium stearate employed in the formulation. The dilution is chosen such that an acceptable shot weight delivered from an inhaler contains exactly the desired dose of active substance. In this regard, the exact dose may be delivered in a single shot or multiple shots. Dilution is also used to affect powder mixtures having good macroscopic properties such as flowability, and to balance adhesive or cohesive forces of the microfine active substance to ensure good homogeneity of the formulation.

The carrier material may be any carrier material that customarily finds use in dry powder formulations. As examples thereof, one can mention mono- or di-saccharides such as glucose, glucose mono-hydrate, lactose, lactose mono-hydrate, sucrose or trehalose; sugar alcohols such as mannitol or xylitol; polylactic acid or cycoldextrin; or mixtures thereof. Preferably lactose mono-hydrate is employed.

Nucleic acids, including double-stranded or single-stranded polynucleotide, oligonucleotide or short nucleic acid sequences may also be formulated according to the present invention. The term nucleic acid includes both RNA (e.g. siRNA, mRNA, ribozymes, aptamers) and DNA (e.g. cDNA or genomic DNA). The nucleic acid may be present in the form of a vector (e.g. a plasmid or other construct) with suitable sequences to direct or control expression (i.e. a promoter sequence).

Carrier materials must be in the form of sufficiently large particle size such that they can be easily handled during manufacture and filling operations. They should also be large enough such that they are not inhalable into the deep lung. Typically a carrier material will have a mean particle diameter (measured as the mass mean aerodynamic diameter) of about 10 to 500 micrometers, and preferably 50 to 300 micrometers.

Dry powder formulations of the present invention are particularly suitable for use in multidose dry powder inhalers. In particular, the formulations are suitable for use in such inhalers, which comprise a reservoir from which individual therapeutic dosages can be withdrawn on demand through actuation of the device. However, formulations of the present invention are also useful in multi-dose inhalers that contain a plurality of capsules containing single or multiple pre-dosed units.

Typical of such multi-dose inhaler device suitable for use with formulations of the present invention is described in U.S. Pat. No. 6,182,655, which is hereby incorporated by reference in its entirety.

The present invention in another of its aspects is directed to such multidose inhalers containing the formulation of the present invention.

Multi-dose inhalers may contain a reservoir of dry powder that contains tens or even hundreds of therapeutic doses. The term "therapeutic dose(s)" as used herein means an amount of inhalation formulation containing a requisite amount of active substance to illicit a therapeutic effect, e.g. to alleviate, prevent or inhibit the particular condition to be treated, when delivered to a patient. A therapeutic dose may be delivered with one or more actuations of a DPI device. This is because the amount of powder that can be delivered to a patient without irritating the patient, e.g. making the patient cough, or what can reasonably or comfortably be delivered within a single inspiration, is limited to about 50 mg per actuation, more particularly 25 mg per actuation. Accordingly, depending on the nature of the active substance and the nature and severity of the condition to be treated, one or more actuations may be necessary per number of hours, per day, for any number of days, weeks, months and so-forth.

The therapeutic dose will depend largely on the nature of the active substance, the condition of the patient, and the nature and severity of the condition to be treated. A therapeutic dose may range between as little as 1 ng/kg, for example when treating a local condition such as asthma with a potent active substance to as much as 10 mg/kg, more particularly dose will range from 20 ng/kg to 1 mg/kg. The therapeutic dose will be indicated on packaging or labeling accompanying the DPI device and is specifically referred to in the Label Claim.

In order to ensure inter-batch quality and reproducibility, formulations should be tested in order to ensure that the mean dose of formulation emitted from a MDI, should not vary considerably from the Label Claim. In this regard, the formulations of the present invention are particularly stable, for example they meet the following standards:

The Mean Delivered Dose is within +/−15% of the Label Claim, and 9 from 10 at least of single doses are not outside +/−25% of the mean, and all single doses are within +/−35% of the mean; or At least 9 from 10 single doses are within +/−20% of the Label Claim, and all single doses are within +/−25% of the Label Claim.

The Shot Weight and Delivered Dose and their variance can be measured using the Dosage Unit Sampling Apparatus (DUSA). The fine particle fraction (FPF) can be measured using an Andersen Cascade Impactor (ACI). The measurement methodology and the apparatus therefore are well known in the art, and are described in the United States Pharmacopoeia Chapter <601>, or in the inhalants monograph of the European Pharmacopoeia, both of which documents are hereby incorporated by reference. The USP states that the Apparatus 1 should be used for the measurement of FPF. The USP also states that Delivered Dose Uniformity should be measured with DUSA or its equivalent. However, the Delivered Dose and Delivered Dose uniformity are preferably measured using the so-called Funnel Method. The Funnel Method is described in *Drug Delivery to the Lungs, VIII* p 116 to 119, which is hereby incorporated by reference. In summary, the Funnel Method consists of discharging a formulation from a DPI into a Funnel Apparatus, which basically consists of a standard Buchner Funnel. The discharged dose is captured on the glass sinter of the Funnel, and can be washed off, and the dose determined using HPLC analysis. The Funnel Method gives comparable results to the standard USP apparatus, and is generally considered to be an equivalent of the DUSA apparatus.

Fine particle fraction measured according to the above described methodology is considered to consist of the combined fractions collected from stages 2 to Filter Stage of an Andersen Cascade Impactor calibrated at 60 L/min air flow rate. These fractions have an aerodynamic particle size of less than 4.7 micrometers.

Alternatively, Fine Particle Fraction can be measured by the Twin Impinger Method and the Multi-stage Liquid Impinger Method as are described in the Pharmacopoea, and as are set forth in the Examples below Formulations of the present invention meet pharmacopoeia requirements as to Delivered Dose Uniformity as set forth, for example in the United States and European Pharmacopoeias. For example, formulations of the present invention meet the requirement set out in the USP26-NF21 chapter <601> "Delivered Dose Uniformity". Indeed, the formulations appear to be so stable that they may even meet the relatively more stringent Delivered Dose Uniformity requirements set forth in the current Draft Guidance from the FDA, published by the CDER in October 1998.

Still further, the Delivered Dose of the formulations contains a high fraction of fine particles, i.e. particles that are capable of penetrating the deep lung, e.g. having a diameter of less than about 4.7 microns, as measured by the ACI; below 6.4 as measured by the Twin Impinger; and below 6.8 as measured by the Multi-stage Liquid Impinger.

Preferred features for the second and subsequent aspects of the invention are as for the first aspect mutatis mutandis.

There now follows a series of examples that serve to illustrate the invention.

Method

Particle Fraction Size Measurement Method

Assemble the Andersen Cascade Impactor according to manufacturer's instructions with a suitable filter in place and ensure that the system is airtight. To ensure efficient particle capture, coat each plate with a high viscosity liquid deposited from a volatile solvent. The pre-separator should be coated in the same way or should contain 10 ml of a suitable solvent. Connect the apparatus to a flow system comprising flow control valve, two-way valve, timer and vacuum pump.

The test is conducted at a flow rate adapted to the internal resistance of the inhaler device drawing 4 liters of air through the apparatus. At high flow rates it may be necessary to remove the lowest stages from the stack. For adjustment of the flow rate connect a flow meter, calibrated for the volumetric flow leaving the meter, to the induction port. Adjust the flow control valve to achieve steady flow through the system at the required rate. Ensure that critical flow occurs in the flow control valve by measuring the absolute pressure on both sides of the flow control valve. Switch off the airflow.

Prepare the dry-powder inhaler for use according to the patient instructions. With the pump running and the two-way valve closed, locate the mouthpiece of the inhaler in the mouthpiece adapter. Discharge the powder into the apparatus by opening the valve for the time required for drawing 4 liters of air through. Repeat the discharge sequence. The number of discharges should be minimised and typically would not be greater than ten. The number of discharges should be sufficient to ensure an accurate and precise determination of fine particle dose. After the final discharge, wait for 5 s and then switch off the pump.

Dismantle the apparatus. Carefully remove the filter and extract the active ingredient into an aliquot of the solvent. Remove the pre-separator, induction port and mouthpiece adapter from the apparatus and extract the drug into an aliquot of the solvent. Extract the active ingredient from the inner walls and the collection plate of each of the stages of the apparatus into aliquots of solvent. Using a suitable method of analysis, determine the quantity of active ingredient contained in each of the nine volumes of solvent.

Calculate the mass of active ingredient deposited on each stage per discharge and the mass of active ingredient per discharge deposited in the induction port, mouthpiece adapter and where used the pre-separator. The total mass of the active ingredient is not less than 75 percent and not more than 125 percent of the average delivered dose determined during testing for uniformity of delivered dose. If the total mass is outside this range the test must be repeated.

Starting at the filter, derive a cumulative mass vs. cut-off diameter of the respective stages. Calculate the Fine Particle Dose (FPD) by interpolation the mass of active ingredient less than 5 μm. If necessary, and where appropriate, plot the cumulative fraction of active ingredient versus cut-off diameter on log probability paper, and use this plot to determine values for the Mass Median Aerodynamic Diameter (MMAD) and the Geometric Standard Deviation (GSD).

EXAMPLE 1

Formulation 1

A dry powder formulation consisting of 2.5% w/w salbutamol sulphate, 2.0% w/w magnesium stearate, and 95.5% w/w lactose monohydrate.

All ingredients are screened through a 180 micron sieve before blending.

Magnesium stearate and lactose monohydrate are mixed in a Turbula T2C powder blender and 62 rpm for 20 minutes.

Active substance is added to 20% of the magnesium stearate-lactose blend in the blender and the mixture mixed for a further 20 minutes at 62 rpm.

The remaining magnesium stearate-lactose blend is added and the mixture blended for a further 20 minutes at 62 rpm in the blender.

Formulation 2

A dry powder formulation consisting of 4% w/w budesonide; 95% w/w Lactose monohydrate; and 1% magnesium stearate. The blending operation is identical to that described for formulation 1.

The powder blends thus produced may be filled into SkyePharma proprietary dry powder inhalers Skyehaler™ as more fully described in U.S. Pat. No. 6,182,655 for assessment of Dose Content Uniformity and fine particle fraction of the delivered dose.

EXAMPLE 2

Particles of the Formulation 1 of Example 1 are scattered and glued onto a carbon tape and shadowed with gold/platinum. Back scattered electron micrographs and X-ray mapping are then carried out using They are then analysed on a StereoScan 360 Scanning Electron Microscope/EDX.

BSE and X-ray mapping analysis shows only very localized coverage of magnesium stearate and a very low surface coverage (less than 10%).

EXAMPLE 3

Measurement of Fine Particle Fraction

The formulations 1 and 2 employed are those formed according to Example 1 above.

After filling the formulations in the DPI devices, the devices are allowed to stand for at least 24 hours before testing.

The aerodynamic particle size distribution of Formulation 1 is determined using Twin Impinger at 60 L/min flow rate (apparatus A of the Eur. Pharmacopoeia 4.4 section 2.9.18). The effective cut-off diameter for stage 3 of this apparatus collecting the fine particle fraction is 6.4 microns. The fine particle dose is the amount of drug that is found in the lower impingement chamber of this apparatus (stage 2).

The aerodynamic particle size distribution of the Formulation 2 is determined using a Multi Stage Liquid Impinger at 60 L/min flow rate (Apparatus C of the Eur Pharmacopoeia 4.4 section 2.9.18). The effective cut-off diameter for stage 3 of this apparatus is 6.8 microns. The fine particle dose is calculated by determining and adding the amount of drug found on stage 3,4 and the filter stage.

10 shots of the formulations of Example 1 are discharged into the particle sizing apparatus specified above at a set flow rate of 60 L/min. Delivered and aerosolised drug particles are classified in accordance with their particle momentum achieved in the flow which depends on the equivalent aerodynamic particle size. Thus fractions of the dose are deposited at different parts or collecting stages of the apparatus, in accordance with the aerodynamic particle size of the drug particles. Each fraction is collected, adjusted to volume and analysed using HPLC.

HPLC analysis of Formulation 1 showed that the fine particle fraction (less than 6.4 microns) of the dose delivered to the Twin Impinger apparatus is about 37%.

HPLC analysis of Formulation 2 showed that the fine particle fraction (less than 6.8 microns) of the dose delivered to the Multi-Stage apparatus is about 32%.

EXAMPLE 4

Effects of Method of Mixing or Blending the Dry Powders is Examined

Comparative Examples are prepared by mixing the ingredients of Formula 1 and ingredients of Formula 2 under high shear mixing conditions according to the following representative methodology:

Lactose and magnesium stearate are mixed in a higher shear mixer (Aeromatic-Fielder PP1) at 600 rpm for 6 minutes. Thereafter the active substance is added to the mixer and the whole is mixed for a further 6 minutes at 600 rpm.

These comparative formulations are filled into DPI devices as defined above and the fine particle fraction of the delivered doses determined as in Example 3 using the Multi Stage Liquid Impinger at 60 L/min flow rate (Apparatus C).

For both formulations, HPLC analysis shows fine particle fraction of less than 20%.

EXAMPLE 5

The formulation 1 of Example 1 is tested for Fine Particle Fraction according to the appropriate method for Formulation 1 defined in Example 3. As comparative examples, powder blends are produced substantially as described in Formulation 1, except the magnesium stearate is omitted, and the mass is made up with lactose.

The formulation 1 and comparative formulation are stored for 24 hours before taking fine particle fraction measurements. The formulations are kept in open storage for the duration of the experiment. The first measurement after this period is consider time=0. Similar measurements are carried out on DPI devices at weekly intervals up to 6 weeks. During the test period the formulations are stored at 40° C. and 75% r.h.

At Time=0, the fine particle fraction of the formulation 1 containing magnesium stearate is about 37%. For the comparative formulation, the fine particle fraction is practically the same at 38%. However, whereas for the formulation containing magnesium stearate the fine particle fraction does not differ by more than about 2% over the test period, the fine particle fraction of the formulation containing no magnesium stearate is reduced by more than 25% in the first week, and by about 50% over the course of the test period.

The results demonstrate the stabilising effect of magnesium stearate on the fine particle fraction dry powder formulations. However, it is interesting that there is practically no difference in the fine particle fraction of the two formulations at time=0. This is possibly an indication that the surface coverage of magnesium stearate is so low that it plays practically no role in affecting the adhesive properties of the active substance to the carrier.

What is claimed is:

1. A dry powder inhaler device comprising a stable dry powder formulation for inhalation, the powder comprising active particles and carrier particles for supporting the active particles, the formulation further comprising magnesium stearate in an amount of at least 0.5% by weight of the formulation, wherein the particles of magnesium stearate are disposed on the surface of the carrier particles to provide a surface coverage of less than 5% on the carrier particles.

2. The dry powder inhaler device of claim 1, wherein the magnesium stearate is present in an amount of from 0.5 to 2% by weight.

3. The dry powder inhaler device of claim 1, wherein the magnesium stearate is present in an amount of from 0.6 to 1% by weight.

4. The dry powder inhaler device of claim 1, wherein the active particles comprise an active substance selected from the group consisting of beta-mimetics, anticholinergics, corticosteroids, leukotriene antagonists, phosphodiesterase inhibitors, PAF-inhibitors, potassium channel openers, analgesics, potency agents, macromolecules, pharmaceutically acceptable salts thereof and mixtures thereof.

5. The dry powder inhaler device of claim 1, wherein the carrier particles comprise a carrier material selected from monosaccharides, disaccharides, sugar alcohols, polylactic acid, or mixtures thereof.

6. The dry powder inhaler device of claim 5, wherein the carrier material is lactose mono-hydrate.

7. The dry powder inhaler device of claim 4, wherein the beta-mimetic is selected from the group consisting of Levalbuterol, Terbutalin, Reproterol, Salbutamol, Salmeterol, Formoterol, Fenoterol, Clenbuterol, Bambuterol, Tulobuterol, Broxaterol, Epinephrin, Isoprenaline and Hexoprenaline.

8. The dry powder inhaler device of claim 4, wherein the anticholinergic is selected from the group consisting of Tiotropium, Ipratropium, Oxitropium and Glycopyrronium.

9. The dry powder inhaler device of claim 4, wherein the corticosteroid is selected from the group consisting of Butixocart, Rofleponide, Budesonide, Ciclosenide, Mometasone, Fluticasone, Beclomethasone, Loteprednol and Triamcinolone.

10. The dry powder inhaler device of claim 4, wherein the leukotriene antagonist is selected from the group consisting of Andolast, Iralukast, Pranlukast, Imitrodast, Seratrodast, Zileuton, Zafirlukast and Montelukast.

11. The dry powder inhaler device of claim 4, wherein the phosphodiesterase-inhibitor is selected from Filaminast or Piclamilast.

12. The dry powder inhaler device of claim 4, wherein the PAF-inhibitor is selected from the group consisting of Apafant, Forapafant and Israpafant.

13. The dry powder inhaler device of claim 4, wherein the potassium channel opener is selected from Amiloride or Furosemide.

14. The dry powder inhaler device of claim 4, wherein the analgesic is selected from the group consisting of Morphine, Fentanyl, Pentazocine, Buprenorphine, Pethidine, Tilidine, Methadone and Heroin.

15. The dry powder inhaler device of claim 4, wherein the potency agent is selected from the group consisting of Sildenafil, Alprostadil and Phentolamine.

16. The dry powder inhaler device of claim 4, wherein the macromolecule is selected from the group consisting of proteins, peptides, oligopeptides, polypeptides, polyamino acids, nucleic acids, polynucleotides, oligo-nucleotides and high molecular weight polysaccharides.

17. The dry powder inhaler device of claim 5, wherein the monosaccharide or disaccharide is selected from the group consisting of glucose, lactose, lactose monohydrate, sucrose, trehalose and mixtures thereof.

18. The dry powder inhaler device of claim 5, wherein the sugar alcohol is selected from mannitol, xylitol, or a mixture thereof.

* * * * *

UNITED STATES PATENT AND TRADEMARK OFFICE
CERTIFICATE OF CORRECTION

PATENT NO. : 8,414,867 B2  
APPLICATION NO. : 13/588655  
DATED : April 9, 2013  
INVENTOR(S) : Rudi Mueller-Walz et al.

Page 1 of 1

It is certified that error appears in the above-identified patent and that said Letters Patent is hereby corrected as shown below:

On the Title Page, at the Related U.S. Application Data, item (60) please correct the filing date of PCT/IB2004/003804 from April 11, 2004 to read "November 4, 2004"

Signed and Sealed this  
Eleventh Day of June, 2013

Teresa Stanek Rea  
*Acting Director of the United States Patent and Trademark Office*